United States Patent [19]

Otomo et al.

[11] Patent Number: 5,886,023
[45] Date of Patent: Mar. 23, 1999

[54] AGENT FOR IMPROVING DEMENTIA

[75] Inventors: Eiichi Otomo; Yoshiyuki Takasu; Tadashi Shiotani; Kazuo Hasegawa; Akira Honma, all of Tokyo, Japan

[73] Assignee: Daiichi Pharmaceutical Co., Ltd., Tokyo, Japan

[21] Appl. No.: 447,054

[22] Filed: May 22, 1995

Related U.S. Application Data

[63] Continuation of Ser. No. 302,047, Sep. 7, 1994, abandoned, which is a continuation of Ser. No. 163,727, Dec. 9, 1993, abandoned, which is a continuation of Ser. No. 876,095, Apr. 30, 1992, abandoned.

[30] Foreign Application Priority Data

May 2, 1991 [JP] Japan ................................. 3-229818
May 2, 1991 [JP] Japan ................................. 3-229819

[51] Int. Cl.$^6$ ................................................. A61K 31/40
[52] U.S. Cl. ............................................................ 514/424
[58] Field of Search .............................................. 514/424

[56] References Cited

U.S. PATENT DOCUMENTS

| | | | |
|---|---|---|---|
| 4,341,790 | 7/1982 | Betzing et al. | 514/424 |
| 4,385,053 | 5/1983 | Reisberg | 424/199 |

FOREIGN PATENT DOCUMENTS

| | | | |
|---|---|---|---|
| 0314275 | 5/1989 | European Pat. Off. | A61K 31/40 |
| 0408524 | 1/1991 | European Pat. Off. | C07D 207/27 |
| 2382441 | 9/1978 | France | C07D 207/26 |
| 2053909 | 2/1981 | United Kingdom | C07D 207/27 |

OTHER PUBLICATIONS

Oslo et al "Remington's Pharmaceutical Sciences" (1980) pp. 1554–1557.
Handbook of Pharmaceutical Excipients (1986) pp. 134–137.

Advances in Behavioral Biology, vol. 38B, 1990, pp. 367–370; H. Kojima et al.: "Effect of DM–9384, A New Pyrrolidone Derivative, on Passive Avoidance and Cerebral Choline Acetyltransferase Activity in Rats".

Advances in Behavioral Biology, vol. 38B, 1990, pp. 371–374; T. Kameyama et al.: "DM–9384, A Pyrrolidone Derivative, Ameliorates Basal Forebrain Lesion–induced Amnesia and Inhibits Cycloheximide–induced Decrease in the Number of GABA and Acetylcholine Receptors".

Advances in Alzhimer Disease Therapy Series, 1991, pp. 337–344, (editors R. Becker et al.), Birkhäuser, Boston, Mass., US, M. Yoshida: "alzheimer Therapy with Cholinomimetics: Japanese Experience".

Pharmacology Biochemistry & Behavior, vol. 36, No. 2, 1990, pp. 233–236, Pergamon Press Plc, US; T. Nabeshima et al.: "Effects of DM–9382, a Pyrrolidone Derivative, on Alcohol–and Chlordiazepoxide–induced Amnesia in Mice".

Advances in Behavioral Biology, vol. 38A, 1990, pp. 735–738; C. Hara et al.: "Characteristics of Learning Deficit Induced by Ibotenic Acid Lesion of the Frontal Cortex Related with the Nucleus Basalis of Meynert in Rats".

*Primary Examiner*—Raymond Henley, III
*Attorney, Agent, or Firm*—Sughrue, Mion, Zinn, Macpeak & Seas, PLLC

[57] ABSTRACT

The present invention aims at providing a drug which is highly effective in improving decline of mental functions such as disorientation, which are the major symptoms of dementia such as Alzheimer type dementia or cerebrovascular dementia, as well as general side symptoms such as decreased spontaneity, contact disturbances, motivation, emotional disturbances, abnormal behaviors and disturbances in activity of daily living. The agent for improving dementia of the present invention comprises N-(2,6-dimethylphenyl)-2-(2-oxo-1-pyrrolidinyl)acetamide or a salt thereof as an active ingredient.

24 Claims, No Drawings

AGENT FOR IMPROVING DEMENTIA

This is a continuation of application Ser. No. 08/302,047, filed Sep. 7, 1994, now abandoned, which is a continuation of application Ser. No. 08/163,727, filed Dec. 9, 1993, now abandoned which is a continuation application of Ser. No. 07/876,095, filed Apr. 30, 1992 now abandoned.

FIELD OF THE INVENTION

This invention relates to an agent for improving dementia which contains N-(2,6-dimethylphenyl)-2-(2-oxo-1-pyrrolidinyl) acetamide (hereinafter, referred to as compound A) represented by the following formula (I):

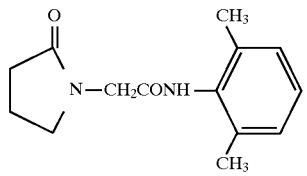

or a salt thereof as an active ingredient.

BACKGROUND OF THE INVENTION

In developed countries including Japan, United States and European countries, the number of patients with dementia has been rapidly increasing with the sudden increase in aged population. Since there is no effective therapeutics for this disease, it is a serious social problem to treat and attend on these patients. Under these circumstances, a number of drugs have been examined in order to develop an effective remedy for dementia. However, no drug which is clinically usable therefor has been found out hitherto.

On the other hand, it is known that compound A is effective in prolonging the survival time upon a decrease in blood oxygen level and in relieving failure of memory due to cerebropathy, as described in JP-B-62-5404 (the term "JP-B" as used herein means an "examined Japanese patent publication") (corresponding to U.S. Pat. No. 4,341,790). However, there has been never reported that the compound A is clinically usable for improving the symptoms of dementia.

SUMMARY OF THE INVENTION

The present inventors have found out that the administration of the compound A to patients with dementia such as Alzheimer type dementia or cerebrovascular dementia causes excellent effects of improving the symptoms of these types of diseases, which had never been expected from the conventional therapeutics, thus completing the present invention.

The present invention relates to an agent for improving dementia which contains compound A or a salt thereof as an active ingredient.

DETAILED DESCRIPTION OF THE INVENTION

Demetia relating to the present invention can be mainly classified into Alzheimer type dementia and cerebrovascular demetia. Alzheimer type dementia may be classified into senile dementia and Alzheimer type disease. It is expected that compound A exerts excellent effects on these diseases.

The compound A may be administered either orally or parenterally (for example, intravenously) in a dose of from 60 to 900 mg/day per adult (in the case of oral administration). Examples of preparations containing compound A include tablets, capsules, pills, emulsions, suspensions, fine subtilaes and injection. These preparations may be formulated by a known pharmaceutical techniques with the use of common additives (for example, fillers, binders (hydroxypropylcellulose, etc.), ingredient (lactose, cornstarch, etc.).

The compound A has a high safety. When orally administered to male and female mice, it showed acute toxicities ($LD_{50}$) of 2,005 mg/kg and 1,940 mg/kg, respectively. Thus it has been clinically confirmed that compound A is highly safe.

The compound A is highly effective in improving a decline in mental functions such as disorientation (place, time), which are the major symptoms of dementia, as well as general side symptoms such as decreased spontaneity, emotional disturbances, contact disturbances, abnormal behaviors, disturbances in activity of daily living and motivation. Accordingly, the compound A is a very excellent agent for improving dementia.

The present invention is further explained in detail hereinafter by the following Examples, but the present invention is not limited to these examples.

EXAMPLE 1

300 mg/day of compound A was orally administered for 8 to 12 weeks to 5 patients (excepting cerebrovascular dementia based on Hachinski cerebro-ischemic score) who showed encephalatrophy or ventricular enlargement in CT (computed tomography) or MRI (magnetic resonance image) and thus were diagnosed as Alzheimer type dementia based on clinical symptoms specified in DSM-III-R (Handbook for the Diagnosis of Mental Diseases prepared by U.S. Society of Psychopathy). Before the administration and 4 weeks, 8 weeks and 12 weeks thereafter, the dementia conditions of these patients were clinically evaluated by typical methods for evaluating dementia, namely, classification of severity by fast staging (hereinafter, referred to simply as Fast), criteria for evaluating cognitive functions (modified GBS), mini-mental state examination (hereinafter, referred to simply as MMS), Hasegawa's simplified dementia scale (hereinafter, referred to simply as HDS) and Crichton's criteria for evaluating behaviors. Based on the data thus obtained, the final global improvement rate (hereinafter, referred to simply as FGIR) and the overall safety rate (hereinafter, referred to simply as OSR) of each case were evaluated.

Table 1 shows the results of FGIR and OSR, while Table 2 shows the number of improved or worsened patients for each symptom. Tables 3 and 4 show each a patient showing improvement in FGIR.

TABLE 1

| Evaluation | No. of Case | I | II | III | IV | V | VI |
|---|---|---|---|---|---|---|---|
| FGIR | 5 | | 2 | | 2 | | 1 |
| OSR | 5 | | | 5 | | | |
| [FGIR] | I: remarkably improved. | | | | | | |
| | II: improved. | | | | | | |
| | III: slightly improved. | | | | | | |
| | IV: unchanged. | | | | | | |
| | V: slightly aggravated. | | | | | | |
| | VI: aggravated. | | | | | | |
| [OSR] | I: no safety problems. | | | | | | |
| | II: negligible safety problems existed. | | | | | | |
| | III: safety problems existed. | | | | | | |
| | IV: significant safety problems existed. | | | | | | |

TABLE 2

Improved or Worsened Item (symptom)

| | No. of Case | Improved | Worsened |
|---|---|---|---|
| Decreased spontaneity | 5 | 2 | 0 |
| Emotional disturbance | 5 | 2 | 1 |
| Contact disturbance | 5 | 2 | 0 |
| Decline in mental function | 5 | 2 | 0 |
| Abnormal behaviors | 5 | 1 | 1 |
| Disturbance in activity of daily living | 5 | 1 | 1 |

TABLE 3

List of Alzheimer type dementia symptoms

| Sex/Age | Dose/Time | Complication/Suffering Period/CT/MRI | Pretreatment/Combined Drug | FAST/Hachinski Cerebro-ischemic Score/MMS/Hasegawa's Scale | FGIR/OSR |
|---|---|---|---|---|---|
| Female/80 | 300 mg/12 weeks | iron-deficiency anemia/2 years/encephalatrophy: slight, and ventricular enlargement: moderate | no/no | 5/1/(11)/13.0 | improved/no safety problem |

| | Evaluation of Cognitive Function | | | | | | |
|---|---|---|---|---|---|---|---|
| | Improvement | | | Severity | | | |
| | 4 week | 8 week | 12 week | (pre | 4 week | 8 week | 12 week) |
| FAST** | | | | ( 5 | 4 | 4 | 4 ) |
| Orientation: | | | | | | | |
| space | III | III | III | ( 2 | 1 | 1 | 1 ) |
| time | III | III | III | ( 4 | 3 | 3 | 3 ) |
| Memory: | | | | | | | |
| private information before outbreak | IV | IV | IV | ( 3 | 3 | 3 | 3 ) |
| private information after outbreak | IV | IV | IV | ( 3 | 3 | 3 | 3 ) |
| Motivation: | | | | | | | |
| endogenous motivation | III | II | II | ( 3 | 2 | 1 | 1 ) |
| exogenous motivation | III | III | III | ( 3 | 2 | 2 | 2 ) |
| Consideration: | | | | | | | |
| suitability of judgement | III | III | III | ( 2 | 1 | 1 | 1 ) |
| development of conversation | IV | IV | IV | ( 3 | 3 | 3 | 3 ) |
| Emotion: | | | | | | | |
| variation of emotional expression | IV | IV | IV | ( 1 | 1 | 1 | 1 ) |
| self-suppression of emotional expression | III | III | III | ( 2 | 1 | 1 | 1 ) |
| Communication: | | | | | | | |
| precision of speaking | III | III | III | ( 3 | 2 | 2 | 2 ) |
| rationality of speaking | IV | IV | IV | ( 1 | 1 | 1 | 1 ) |

| | Pre | | 4 week | | 8 week | | 12 week |
|---|---|---|---|---|---|---|---|
| MMS | 11 | → | 14 | → | 5 | → | 16 |
| HDS | 13.0 | → | 14.5 | → | 15.5 | → | 17.5 |

**: Degree of disorientation II: improved. III: slightly improved. IV: unchanged.

Crichton's Criteria for Behavior (modified)

| | Change | | Side Effect/ | |
|---|---|---|---|---|
| No.* | Pre | 12 Weeks | Abnormal Clinical Data | Comment |
| 1. | 1 → | 1 | no/no | Getting to be able to handle a gas water heater. |
| 2. | 3 → | 2 | | |

TABLE 3-continued

| | | | | |
|---|---|---|---|---|
| 3. | 2 | → | 2 | Making purchases with a memo |
| 4. | 3 | → | 2 | note, as previously, but never |
| 5. | 2 | → | 1 | purchasing any unnecessary goods. |
| 6. | 2 | → | 2 | Frankly stating her opinion. → |
| 7. | 2 | → | 1 | Sometimes boycotting the test |
| 8. | 1 | → | 1 | (refusing writing sentences in |
| 9. | 1 | → | 1 | MM, "I'm weak in writing"). |
| 10. | 2 | → | 1 | The medicine of the invention |
| 11. | 1 | → | 1 | was administered from the first |
| | | | | examination, after confirming |
| | | | | her husband that she had been in |
| | | | | the same conditions for past 2 to |
| | | | | 4 weeks. Although no change was |
| | | | | shown in HDS or MMS score, IADL |
| | | | | suggested obvious improvement. |
| | | | | Improvement in these points can |
| | | | | be hardly evaluated by the |
| | | | | methods employed here. |

*: 1: walking. 2: orientation. 3: conversation. 4: interpersonal contact. 5: unrest. 6: changing clothes. 7: eating. 8: incontinence. 9: sleeping. 10: objective mood. 11: subjective mood.

TABLE 4

List of Alzheimer type dementia symptoms

| Sex/Age | Dose/Time | Complication/ Suffering period/CT/MRI | Pretreatment/ Combined Drug | FAST/Hachinski Cerebro-ischemic Score/MMS/ Hasegawa's Scale | FGIR/OSR |
|---|---|---|---|---|---|
| Female/73 | 300 mg/9 weeks | hepatic function disorder/3 years/ encephalatrophy: slight, and ventricular enlargement: slight | Elen (Trade Mark, Indeloxazine Hydrochloride) (3T)/no | 5/4/18/15.5 | improved/ no safety problem |

| | Evaluation of Cognitive Function | | | | | | |
|---|---|---|---|---|---|---|---|
| | Improvement | | | Severity | | | |
| | 4 week | 8 week | 12 week | (pre | 4 week | 8 week | 12 week) |
| FAST** | | | | (5 | | 5 | ) |
| Orientation: | | | | | | | |
| space | IV | IV | | ( 2 | 2 | 2 | ) |
| time | IV | IV | | ( 4 | 4 | 4 | ) |
| Memory: | | | | | | | |
| private information before outbreak | IV | IV | | ( 3 | 3 | 3 | ) |
| private information after outbreak | IV | IV | | ( 3 | 3 | 3 | ) |
| Motivation: | | | | | | | |
| endogenous motivation | III | III | | ( 3 | 2 | 2 | ) |
| exogenous motivation | II | II | | ( 3 | 1 | 1 | ) |
| Consideration: | | | | | | | |
| suitability of judgement | IV | IV | | ( 1 | 1 | 1 | ) |
| development of conversation | II | II | | ( 3 | 1 | 1 | ) |
| Emotion: | | | | | | | |
| variation of emotional expression | III | III | | ( 3 | 2 | 2 | ) |
| self-suppression of emotional expression | IV | IV | | ( 2 | 2 | 2 | ) |
| Communication: | | | | | | | |
| precision of speaking | IV | IV | | ( 2 | 2 | 2 | ) |
| rationality of speaking | IV | IV | | ( 1 | 1 | 1 | ) |

| | Pre | | 8 week |
|---|---|---|---|
| MMS | 18 | → | 21 |
| HDS | 15.5 | → | 18.5 |

**: Degree of disorientation II: improved. III: slightly improved. IV: unchanged.

TABLE 4-continued

| | Crichton's Criteria for Behavior (modified) | | | | |
|---|---|---|---|---|---|
| | Change | | | Side Effect/ | |
| No.* | Pre | | 12 Weeks | Abnormal Clinical Data | Comment |
| 1. | 1 | → | 1 | no/no | Beginning to give lessons in penmanship to grandchildren spontaneously (feeling tired before the administration). HDS and MMS show little change. Moderate improvement was observed even in a drug-rest period between 4 and 8 weeks. In this case, spontaneousness and positiveness were remarkably improved. No examination was made after 9 week. Having no contact with her family, it seems that the disorders in behaviors have never been worsened. |
| 2. | 3 | → | 3 | | |
| 3. | 2 | → | 2 | | |
| 4. | 2 | → | 1 | | |
| 5. | 1 | → | 1 | | |
| 6. | 1 | → | 1 | | |
| 7. | 1 | → | 1 | | |
| 8. | 1 | → | 1 | | |
| 9. | 1 | → | 1 | | |
| 10. | 2 | → | 1 | | |
| 11. | 2 | → | 1 | | |

*: 1: walking. 2: orientation. 3: conversation. 4: interpersonal contact. 5: unrest. 6: changing clothes. 7: eating. 8: incontinence. 9: sleeping. 10: objective mood. 11: subjective mood.

As the above Tables clearly show, compound A is effective in improving mental symptoms (for example, decreased spontaneity, emotional disturbances, contact disturbances, decline in mental functions, abnormal behaviors) of patients with Alzheimer type dementia. Evaluating the improvement effect on these symptoms, the overall improvement rate of compound A is 40% (2 (improvement case) per 5 all tried case). Also, as apparently from the Table 1, the mental symptoms of 2 cases per 5 cases were not worsened. Furthermore, any side effect was not observed for all tried patients.

Generally, a main characteristic points of patients with Alzheimer type dementia is just that the symptoms of this disease become worse and worse, and any medicines have never showed clinical effects to this disease.

Therefore, these clinical effect of compound A to Alzheimer type dementia, that is, the improvement effect on the symptoms, the suppresing effect on getting worse relating to the symptoms and the effect relating to the safety have never been expected from the clinical effect of convertional medicines for this disease.

EXAMPLE 2

150 to 450 mg/day of compound A was orally administered for 8 weeks to 145 patients with cerebrovascular dementia who showed infarction or hemorrhagic lesions in CT (computed tomography) and scored less than 22 points in Hasegawa's simplified dementia scale (HDS) frequently employed in the simplified diagnosis for dementia. The clinical conditions of each patient were evaluated with HDS, which is frequently used for evaluating the effects of nootropic agents, before the initiation of the administration and 4 weeks and 8 weeks thereafter. Based on these data, the final global improvement rate (FGIR) and the overall safety rate (OSR) were determined.

Table 1 shows the results of FGIR and OSR, while Table 2 shows the improvement rate (%) for each symptom.

TABLE 1

| | No. of Case | I | II | III | IV | V | DP | |
|---|---|---|---|---|---|---|---|---|
| FGIR | 145 | 7 | 37 | 57 | 33 | 5 | 6 | 72.7 [improvement rate (%)*] |
| OSR | 145 | 134 | 8 | 3 | 0 | — | 0 | 97.9 [safety rate (%)**] |

*improvement rate = (I + II + III)/139 × 100
**safety rate = (I + II)/145 × 100
[FGIR] I: remarkably improved. II: moderately improved. III: slightly improved. IV: unchanged. V: aggravated. DP: dropped out.
[OSR] I: no safety problem. II: negligible safety problems existed.

TABLE 2

| Symptom | No. of Case | Improved (%) | Worsened (%) |
|---|---|---|---|
| Decreased spontaneity | 138 | 59.4 | 0.0 |
| Emotional disturbance | 135 | 54.1 | 1.5 |
| Contact disturbance | 122 | 38.5 | 0.8 |
| Decline in mental function | 139 | 46.0 | 2.2 |
| Abnormal behaviors | 49 | 49.0 | 10.2 |

As the above Tables clearly show, compound A is effective in improving mental symptoms (for example, decreased spontaneity, emotional disturbances, contact disturbances, decline in mental functions, abnormal behaviors) of patients with cerebrovascular dementia. The overall improvement rate determined by generally evaluating these results in 72.7%, showing excellent effects.

In general, it is considered that the effects of medicinal treatments on cerebrovascular dementia are inferior to those on sequela of cerebrovascular disorders, namely, the preceding stage of the former. However, compound A achieves a high overall improvement rate (72.7%) for cerebrovascular dementia which is comparable to, or even exceeds, the overall improvement rate (about 70%) of conventional nootropic agent for the sequela of cerebrovascular disorders.

Further, it is doubtful whether or not medicinal treatments are effective on the decline in mental function, i.e., the major symptom of dementia. The overall improvement rate of compound A on this symptom is 46% which is higher than those of pracebo (25%) and other nootropic agent (about 35%).

On the other hand, it has been confirmed that compound A is highly safe (OSR=97.9%) and only fugitive side effects were observed in 4 cases (3%).

These results indicate that compound A is highly superior in the effects of improving cerebrovascular dementia to drugs conventionally employed therefor.

While the invention has been described in detail and with reference to specific embodiments thereof, it will be apparent to one skilled in the art that various changes and modifications can be made therein without departing from the spirit and scope thereof.

What is claimed is:

1. A method for improving mental symptoms of dementia in humans comprising administering to a human being a pharmaceutically effective amount of a composition containing N-(2,6-dimethylphenyl)-2-(2-oxo-1-pyrrolidinyl)acetamide represented by the formula(I):

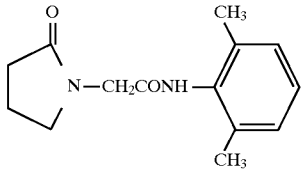

or a salt thereof as an active ingredient.

2. The method as claimed in claim 1, wherein the dementia is Alzheimer's dementia.

3. The method as claimed in claim 1, wherein the dementia is cerebrovascular dementia.

4. The method as claimed in claim 1, wherein the mental symptom is emotional disturbance.

5. The method as claimed in claim 1, wherein the mental symptom is contact disturbance.

6. The method as claimed in claim 1, wherein the mental symptom is decline in mental function.

7. The method as claimed in claim 1, wherein the mental symptom is abnormal behavior.

8. A method for treating a human suffering from mental symptoms of dementia comprising a method for improving mental symptoms of dementia in humans comprising administering to a human being a pharmaceutically effective amount of a composition containing N-(2,6-dimethylphenyl)-2-(2-oxo-1-pyrrolidinyl)acetamide represented by the formula(I):

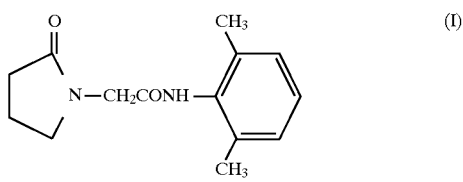

or a salt thereof as an active ingredient.

9. The method as claimed in claim 8, wherein the dementia is Alzheimer's dementia.

10. The method as claimed in claim 8, wherein the dementia is cerebrovascular dementia.

11. The method as claimed in claim 8, wherein the mental symptom is emotional disturbance.

12. The method as claimed in claim 8, wherein the mental symptom is contact disturbance.

13. The method as claimed in claim 8, wherein the mental symptom is decline in mental function.

14. The method as claimed in claim 8, wherein the mental symptom is abnormal behavior.

15. The method as claimed in claim 9, wherein the mental symptom is emotional disturbance.

16. The method as claimed in claim 9, wherein the mental symptom is contact disturbance.

17. The method as claimed in claim 9, wherein the mental symptom is decline in mental function.

18. The method as claimed in claim 9, wherein the mental symptom is abnormal behavior.

19. The method as claimed in claim 10, wherein the mental symptom is emotional disturbance.

20. The method as claimed in claim 10, wherein the mental symptom is contact disturbance.

21. The method as claimed in claim 10, wherein the mental symptom is decline in mental function.

22. The method as claimed in claim 10, wherein the mental symptom is abnormal behavior.

23. The method of claim 1, comprising administering an oral dose of from 60 to 900 mg/day.

24. The method of claim 8, comprising administering an oral dose of from 60 to 900 mg/day.

* * * * *